United States Patent
Tajima

[19]

[11] Patent Number: 6,123,903
[45] Date of Patent: Sep. 26, 2000

[54] CHEMILUMINESCENCE MEASURING APPARATUS

[75] Inventor: Hideji Tajima, Tokyo, Japan

[73] Assignee: Precision System Science Co., Ltd., Tokyo, Japan

[21] Appl. No.: 08/983,443

[22] PCT Filed: Jul. 10, 1997

[86] PCT No.: PCT/JP96/01918

§ 371 Date: Jan. 9, 1998

§ 102(e) Date: Jan. 9, 1998

[87] PCT Pub. No.: WO97/03349

PCT Pub. Date: Jan. 30, 1997

[30] Foreign Application Priority Data

Jul. 10, 1995 [JP] Japan .................................. 7-195736

[51] Int. Cl.⁷ .................................................. G01N 21/76
[52] U.S. Cl. ...................... 422/52; 422/82.08; 250/361 C
[58] Field of Search ................................. 422/52, 82.08; 250/361 C

[56] References Cited

U.S. PATENT DOCUMENTS

| | | | |
|---|---|---|---|
| 3,520,660 | 7/1970 | Webb | 422/52 |
| 4,755,055 | 7/1988 | Johnson et al. | 422/52 |
| 5,290,513 | 3/1994 | Berthold et al. | 422/52 |
| 5,447,687 | 9/1995 | Lewis et al. | 422/52 |
| 5,682,232 | 10/1997 | Tajima et al. | 422/52 |

FOREIGN PATENT DOCUMENTS

| | | |
|---|---|---|
| 3-095951 | 9/1991 | Japan . |
| 5-215681 | 8/1993 | Japan . |
| 5-249029 | 9/1993 | Japan . |

*Primary Examiner*—Jeffrey Snay
*Attorney, Agent, or Firm*—McDermott, Will & Emery

[57] ABSTRACT

This invention provides a measuring apparatus that allows measurements of light in various inspections based on different light generating principles to be performed by a single measuring apparatus and thus widens the range of reagents that can be used, increasing the versatility of this single measuring apparatus and significantly enhancing its usefulness for users and reagent manufacturers. The measuring apparatus of this invention comprises: a light receiving unit and/or a light receiving unit holder connected to a light measuring device; a nozzle holder holding a nozzle for injecting reagents including luminescent reagents into a container; and a container containing a specimen and/or a container holder; wherein the container or container holder and the light receiving unit or light receiving unit holder, and/or the nozzle holder are coupled together to form an enclosed space shielded from external light.

15 Claims, 3 Drawing Sheets

CHEMILUMINESCENCE MEASURING APPARATUS

BACKGROUND OF THE INVENTION

1. Field of the Invention

The present invention relates to a measuring apparatus suitably applied to immunoassays and various medical inspections based on the chemical luminescence method and to biochemical reactions. More specifically it relates to a measuring apparatus which can perform two types of assays in a single inspection equipment, a chemical luminescence immunoassay (CLIA) in which a target substance emits light immediately after being supplied a trigger reagent and a chemical luminescence enzyme immunoassay (CLEIA) in which the amount of light from a target substance stabilizes a predetermined time after reaction with a substrate.

2. Description of Related Art

As is known, the immunoassay based on the chemical luminescence has the advantage of a very high sensitivity and thus a high measurement reliability. As to light generation, there are a variety of principles, such as one which produces luminescence immediately after the supply of a trigger reagent as in CLIA and one which produces a stabilized amount of light a predetermined time after reaction with a substrate as in CLEIA. Depending on the light generating principle used, a luminous reagent may or may not need to be supplied during the light intensity measurement. Hence, the mechanism of the apparatus varies according to the light generating method adopted.

Further, in the case of immunoassays based on the chemical luminescence method, because light must be strictly shielded during the measurement of light, it is practically impossible for a single test equipment to perform immunoassays with different light measuring principles under a strict light shielding condition. For this reason, it has been required that a dedicated automatic inspection apparatus be used that performs only those assays based on the same light measuring principle.

The present invention has been accomplished under these circumstances and has the following objectives.

It is a first object of this invention to provide an improved measuring apparatus.

It is a second object of this invention to provide a measuring apparatus with versatility which allows a single test equipment to perform different types of assays that are based on different light generating principles or use a variety of reagents.

It is a third object of this invention to provide a reliable measuring apparatus which can perform assays in a strictly shielded atmosphere with high precision, efficiently and swiftly.

It is a fourth object of this invention to provide a measuring apparatus which allows performance of assays with simple operations and has good operability.

It is a fifth object of this invention to provide a measuring apparatus which is simple in construction and inexpensive.

SUMMARY OF THE INVENTION

To achieve these objectives, the measuring apparatus according to the first aspect of this invention comprises: a light receiving unit and/or a light receiving unit holder connected to a light measuring device; a nozzle holder holding a nozzle for injecting reagents including luminescent reagents into a container; and a container containing a specimen and/or a container holder; wherein the container or container holder and the light receiving unit or light receiving unit holder, and/or the nozzle holder are coupled together to form an enclosed space shielded from external light.

Here, the reason that the phrase "a light receiving unit and/or a light receiving unit holder" is used is that the light receiving unit and the light receiving unit holder are handled as separate members in one case and as one integral member in another case.

Likewise, the phrase "a container and/or a container holder" is used because they are separate members in one case and the container itself serves as its holder in another case.

The word "and/or" means that the enclosed space is formed in one case by the light receiving unit or its holder, the nozzle holder and the container or its holder, all coupled together, and in another case by the light receiving unit or its holder and the container or its holder.

Because the reagent, the light receiving unit or the nozzle are enclosed in a light-shielded space, weak light produced by the reagent and luminescent reagent can be thrown into the light measuring device without leakage and at the same time external light can be shielded reliably. Hence, measurements such as immunoassays can be made with high sensitivity and reliability.

A second aspect of this invention is that, in the first aspect, the container or container holder, the light receiving unit or light receiving unit holder, and the nozzle holder are each coated with a light shielding film or made of an opaque material with an excellent light shielding characteristic or applied with a color with an excellent light shielding characteristic, or they are installed in a dark room or box, or these light shielding means are combined.

Because the container, the light receiving unit or its holder, and the nozzle holder are shielded against light, reliable measurements can be made with external light kept from entering.

A third aspect of this invention is that, in the first or second aspect, a coupling portion between the container or container holder and the light receiving unit or light receiving unit holder, or between the container or container holder and the nozzle holder, and a coupling portion between the nozzle holder and the light receiving unit or light receiving unit holder are provided with a light shielding packing.

The provision of the light shielding packing in the coupling portion between the container and the light receiving unit reliably prevents leakage of light from inside or entrance of external light at the connected portion, assuring sensitive and reliable measurements.

A fourth aspect of this invention is that in the first to third aspect, the container, the nozzle holder or the light receiving unit holder is coated with a reflective film or made of a material with an excellent reflection characteristic, or an inner wall of the container, the nozzle holder or the light receiving unit holder is applied with a color, such as white, with an excellent reflection characteristic, or these reflection means are combined.

Because the light produced in the container is not absorbed by the inner wall of the container but reflected, weak light can be picked up efficiently and without leakage, thus assuring measurements with high sensitivity.

A fifth aspect of this invention is that, in the first to fourth aspect, the measuring apparatus further comprises a holder mounting device for mounting and dismounting, according to an inspection to be performed, the nozzle holder to and from between the light receiving unit or light receiving unit holder and the container or container holder; wherein when the nozzle holder is mounted, the light receiving unit or light receiving unit holder, the nozzle holder, and the container or container holder are coupled together to form an enclosed space; wherein when the nozzle holder is dismounted, the light receiving unit or light receiving unit holder and the container or container holder are coupled together to form an enclosed space.

This aspect of the invention enables a variety of kinds of inspections with or without the use of luminescent reagent, making the measuring apparatus very versatile.

A sixth aspect of this invention is that, in the first to fifth aspect, when the inspection to be performed is a chemical luminescence immunoassay, the nozzle holder holding a nozzle for injecting a trigger reagent is mounted, and when the inspection is a chemical luminescence enzyme immunoassay that measures light produced by an enzyme-substrate liquid reaction, the nozzle holder is dismounted.

A seventh aspect of this invention is that, in the first to sixth aspect, the nozzle holder is provided with a plurality of nozzles.

This allows injection of a variety of reagents, further increasing the versatility of the measuring apparatus.

An eighth aspect of this invention is that, in the first to seventh aspect, the measuring apparatus further comprises a container transfer device for transferring the container.

This makes it possible to replace the container efficiently without human intervention and thereby perform a variety of kinds of measurements.

A ninth aspect of this invention is that, in the first to eighth aspect, a photomultiplier is used as the light measuring device.

A tenth aspect of this invention is that, in the first to ninth aspect, the measuring apparatus further comprises a nozzle holder transfer device for transferring the nozzle holder. This makes it possible to choose from among various nozzle holders and thereby perform a variety of kinds of measurements, further increasing the versatility of the apparatus.

An eleventh aspect of this invention is that, in the first to tenth aspect, the measuring apparatus further comprises an engagement portion provided at an upper end of the container or container holder and adapted to engage a lower end of the light receiving unit or light receiving unit holder or a lower end of the nozzle holder, and an engagement portion provided at an upper end of the nozzle holder and adapted to engage a lower end of the light receiving unit or light receiving unit holder.

This arrangement ensures light shielding and coupling of the coupling portions between the container, the nozzle holder and the light receiving unit or its holder, thus enhancing reliability.

A twelfth aspect of this invention is that, in the first to eleventh aspect, a light transmission means or a light gathering means such as cylindrical lens, or a combination of these is installed, as the light receiving unit, either on an axis of incidence of the light measuring device in the light receiving unit holder or in the nozzle holder.

This allows weak light produced to be reliably thrown into the light measuring device, thus increasing the sensitivity of measurements.

The measuring device according to a thirteenth aspect of this invention comprises: a light shielding case for accommodating a photomultiplier and an optical means disposed on an incident axis of the photomultiplier so that the photomultiplier and the optical means are shielded from light; a nozzle holder shielded from external light, the nozzle holder having an engagement portion at an upper end thereof and a reagent supply nozzle, the engagement portion being adapted to engage a lower end of the light shielding case, the reagent supply nozzle piercing through a side wall of the nozzle holder from outside and reaching a container; and a light-shielded container having an engagement portion at an upper end thereof to engage a lower end of the light shielding case or a lower end of the nozzle holder, the container being formed of a reflective material or applied with a reflective color or coating.

This offers a versatile measuring apparatus that enables a variety of kinds of immunoassays based on different light generating principles and using various reagents to be performed with a single inspection equipment. Further, highly precise measurements can be made in a strictly light-shielded environment. This invention can also offer a measuring apparatus that is easy to handle and operate and which is simple in construction and inexpensive.

A fourteenth aspect of this invention is that, in the thirteen aspect, the optical means is formed by a light transmission means or a light gathering means such as cylindrical lens, or a combination of these.

This enables weak light to be thrown into the light measuring device, assuring efficient and quick measurements.

A fifteenth aspect of this invention is that, in the first to fourteenth aspect, a lower end portion of the light shielding case or the nozzle holder is formed with an annular groove, a packing formed of an annular elastic member is installed in the annular groove, and an upper end portion of the nozzle holder or the container or the container holder is formed with an annular projection to press against the packing.

The packing made of an elastic member is pressed and deformed to fill the groove without any clearance. The pressing portion is shielded from outside against light to exclude any unwanted light from outside and also prevent leakage of light, thus ensuring reliable measurements.

DESCRIPTION OF THE PREFERRED EMBODIMENTS

Now, the present invention will be described in detail in conjunction with the first embodiment shown in the accompanying drawings.

The measuring apparatus of this invention is applied to chemoluminescence type test equipment that employ a light generating technique by which light is produced immediately after a trigger reagent is supplied, like the CLIA method, or one by which the amount of light generated stabilizes a certain time after reaction with a substrate, as in the CLEIA method. More specifically, this measuring apparatus is applied either to test equipment which, before shipping, are assigned one of the assay methods, CLIA or CLEIA, and fixed to the selected method, or to random access type test equipment which, according to the customer's requirements, are made to be able to perform both assay methods in a single test equipment. The embodiment shown represents the measuring apparatus as applied to the random access type test equipment. As to the components making up this test equipment—such as containers, a container transport means, a pipet apparatus for distributing specimens and reagents, and a pipet apparatus transport means—a variety of known devices are available and they may be selected according to test items and processing to be performed. Detailed description on these components are therefore omitted.

Figure 1:
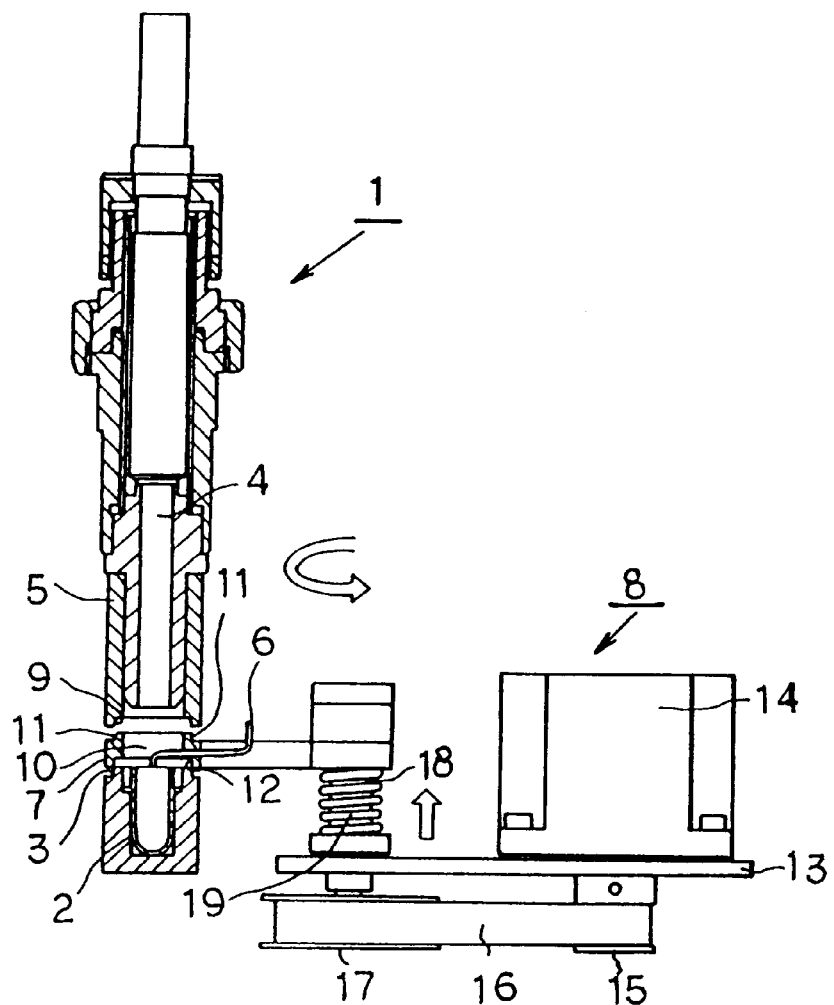
FIG. 1 is a cross section showing a measuring apparatus as one embodiment of this invention in a state before a measurement according to a CLIA method is made.

The measuring apparatus 1 applied to these chemoluminescence type test equipment is arranged at an optical measuring position in the test equipment, as shown in FIG. 1, and accommodates a reagent according to the specimen and the inspection items. A container 2 that has undergone a predetermined reaction is set at the optical measuring position. The container 2 has a circumferential raised portion 3 at the top of the hole protrude upwardly, with its inner surface coated with a light shielding film.

That is, the measuring apparatus 1 that counts the number of photons of a specimen set at the optical measuring position includes, as shown in FIG. 1 to FIG. 4, a photomultiplier (PMT) and cylindrical lens 4a, 4b of known construction; a holder 5 at the lower part of the PMT and cylindrical lens 4a, 4b; a vertical guide mechanism (not shown) for moving the PMT and cylindrical lens 4a, 4b up or down; a reagent nozzle 6 for supplying a predetermined amount of a trigger (hydrogen peroxide H2O2) for the CLIA assay into the container 2 at the optical measuring position; a nozzle holder 7 for holding the reagent nozzle 6; and a nozzle holder drive device 8 for moving the nozzle holder 7 to and from a position between the PMT and cylindrical lens 4a, 4b and the container 2.

The holder 5 is made of a cylindrical body with an excellent light shielding capability, located at the lower part of the PMT and cylindrical lens 4a, 4b. The cylindrical body has an inverted recessed step portion 9 formed at the bottom inner circumference thereof. The holder 5 works as a receptor for cylindrical lens.

The vertical guide mechanism for lifting and lowering the PMT and cylindrical lens 4a, 4b, though not shown, is activated when the container 2 reaches the optical measuring position and, in response to a command from a control system, lowers the PMT and cylindrical lens 4a, 4b. When the measurement is finished, the vertical guide mechanism lifts the PMT and cylindrical lens 4a, 4b to a standby position. The vertical guide mechanism can use one of the known raise/lower mechanisms consisting of a timing belt and a motor.

The PMT 4b corresponds to a light measuring device and the cylindrical lens 4a to a light receiver. Normally, the PMT and the cylindrical lens are handled as one component.

Figure 2:
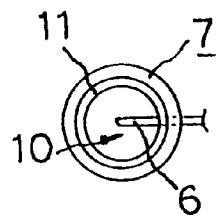
FIG. 2 is an enlarged plan view of a reagent nozzle holder forming a part of the measuring apparatus.

The nozzle holder 7 holding the reagent nozzle 6 in a completely shielded condition has a light transmission hole 10 at the center, as shown in FIG. 2, with an end of the reagent nozzle 6 extending to nearly the center of the light transmission hole 10. The other end of the reagent nozzle 6 is connected to a luminous reagent container not shown.

The nozzle holder 7 is formed with a raised portion 11 at the top that engages with the inverted recessed step portion 9 of the holder 5 and, at the bottom inner circumference, with an inverted recessed step portion 12 that engages with the circumferential raised portion 3 of the container 2.

Figure 3:
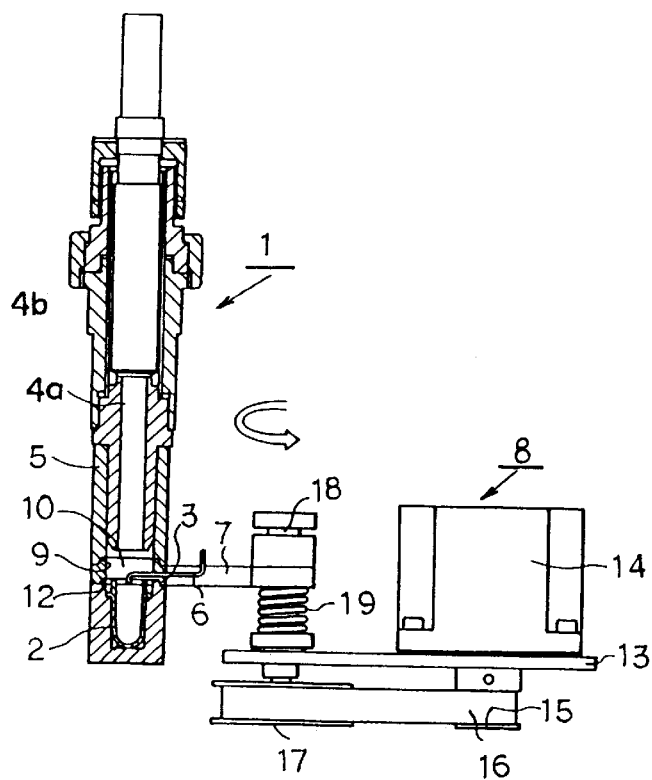
FIG. 3 is a cross section of the measuring apparatus when performing a measurement according to the CLIA method.
Figure 4:
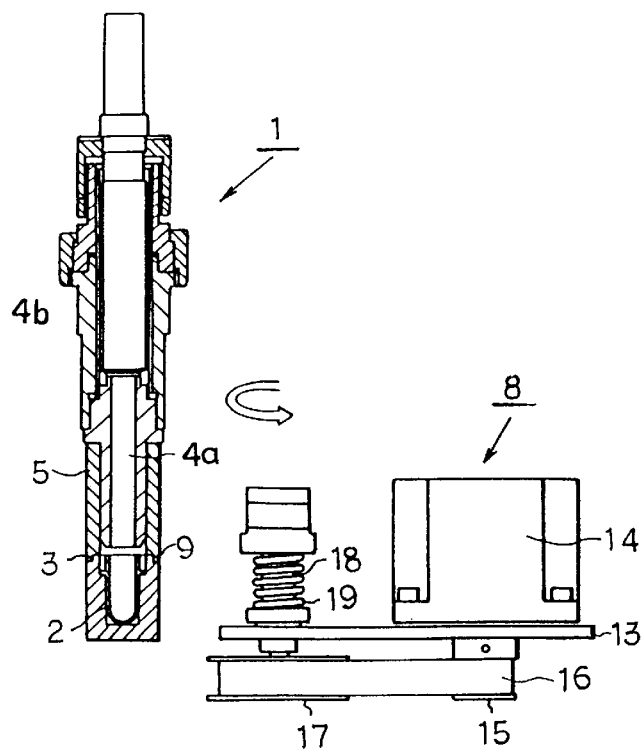
FIG. 4 is a cross section showing a photomultiplier (PMT) and a sample container in their coupled state when a measurement according to the CLEIA method is made.

The nozzle holder drive device 8 for feeding and removing the nozzle holder 7 to and from the position between the PMT and cylindrical lens 4a, 4b and the container 2 according to the measuring method adopted comprises a motor 14 mounted to a base member 13 in the measuring section and a belt 16 wound on a rotating shaft 15 of the motor 14. The belt 16 is wound around the rotating shaft 15 of the motor 14 and a pulley 17. As the motor 14 is rotated forwardly or backwardly, a rotating shaft 18 is turned to feed or retract the nozzle holder 7 to or from the position between the PMT and cylindrical lens 4a, 4b and the container 2. In FIGS. 1, 3 and 4, reference number 19 denotes a coil spring that is wound around the rotating shaft 18 to urge the rotating shaft 18 upwardly at all times.

When a command from the control system dictates a CLIA assay method which produces luminance immediately after a luminous reagent is injected, the measuring apparatus 1 of the above construction activates the motor 14 to feed the nozzle holder 7 to a position between the PMT and cylindrical lens 4a, 4b and the container 2, as shown in FIG. 1.

Then, the vertical guide mechanism is operated to lower the PMT and cylindrical lens 4a, 4b causing the inverted recessed step portion 9 of the holder 5 to engage with the raised portion 11 formed at the top of the nozzle holder 7. In this condition, as the PMT and cylindrical lens 4a, 4b is further lowered, the nozzle holder 7 moves down against the force of the coil spring 19, causing the inverted recessed step portion 12 at the bottom of the nozzle holder 7 to engage with the circumferential raised portion 3 of the container 2, as shown in FIG. 3. At this time, not only are the holder 5, the nozzle holder 7 and the container 2 firmly engaged together in a strict light shielding state but also the reagent nozzle 6 inserted into the nozzle holder 7 is completely shielded so that no light enters inside.

After the nozzle holder is set in this state, the control system activates the pump of the reagent nozzle 6 to inject a predetermined amount of the trigger (hydrogen peroxide H2O2), a luminous reagent, into the specimen in the container 2.

The specimen immediately produces chemical luminance, whose light passes through the light transmission hole 10 of the nozzle holder 7 and the cylindrical lens 4a into the PMT 4b where its intensity is measured.

After this measurement is taken, the vertical guide mechanism is driven upward allowing the nozzle holder 7 to move upward by the force of the coil spring 19 to the home position, disengaging the inverted recessed step portion 9 of the holder 5 from the raised portion 11 of the nozzle holder 7 and also the inverted recessed step portion 12 of the nozzle holder 7 from the circumferential raised portion 3 of the container 2.

When a command from the control system dictates a CLEIA assay method, in which the light intensity stabilizes a predetermined time after reaction with a substrate, the measuring apparatus 1 sets the nozzle holder 7 in a standby position, not interposed between the PMT and cylindrical lens 4a, 4b and the container 2, as shown in FIG. 4, a predetermined time after the luminous substrate liquid was injected into the container 2. With the nozzle holder 7 held in the standby position, the control system activates only the vertical guide mechanism to lower the PMT and cylindrical lens 4a, 4b.

This causes the inverted recessed step portion 9 of the holder 5 to engage with the circumferential raised portion 3 of the container 2 in a perfect light shielding state. Then, in this shielded condition the PMT 4b measures light of the specimen in the container 2 for a specified length of time.

After this measurement is complete, the vertical guide mechanism moves up releasing the inverted recessed step portion 9 of the holder 5 and the circumferential raised portion 3 of the container 2 from the engaged state.

While the above embodiment has described an example case where the container 2, holder 5 and nozzle holder 7 are shielded against light by coating a light-shielding film, this invention is not limited to this embodiment but various modifications may be made. For example, it is possible to form these members from an opaque material with an excellent light shielding capability or coat them with a light-shielding color, or use these means in combination. When the container 2 is transparent, the above light-shielding means can be applied to the container holder (not shown) that holds the container 2 erect, for reliable light-shielding effects.

This invention can also be applied to testing equipment that perform a combination of immunoassays with different light emitting principles, one requiring injection of a luminous reagent during the measurement of light and the other not requiring it.

Further, while the above embodiment has described the nozzle holder to be held in a standby position away from the inserted position between the PMT and cylindrical lens 4a, 4b and the container 2 when performing the CLEIA immunoassay, it is also possible with this invention to feed the nozzle holder 7 to the inserted position between the PMT and cylindrical lens 4a, 4b and the container 2, as in the operation and control for the CLIA method, and not to perform only the injection of the luminous reagent from the reagent nozzle 6. This produces the similar effect and offers the advantage of being able to simplify the control software.

Figure 5:
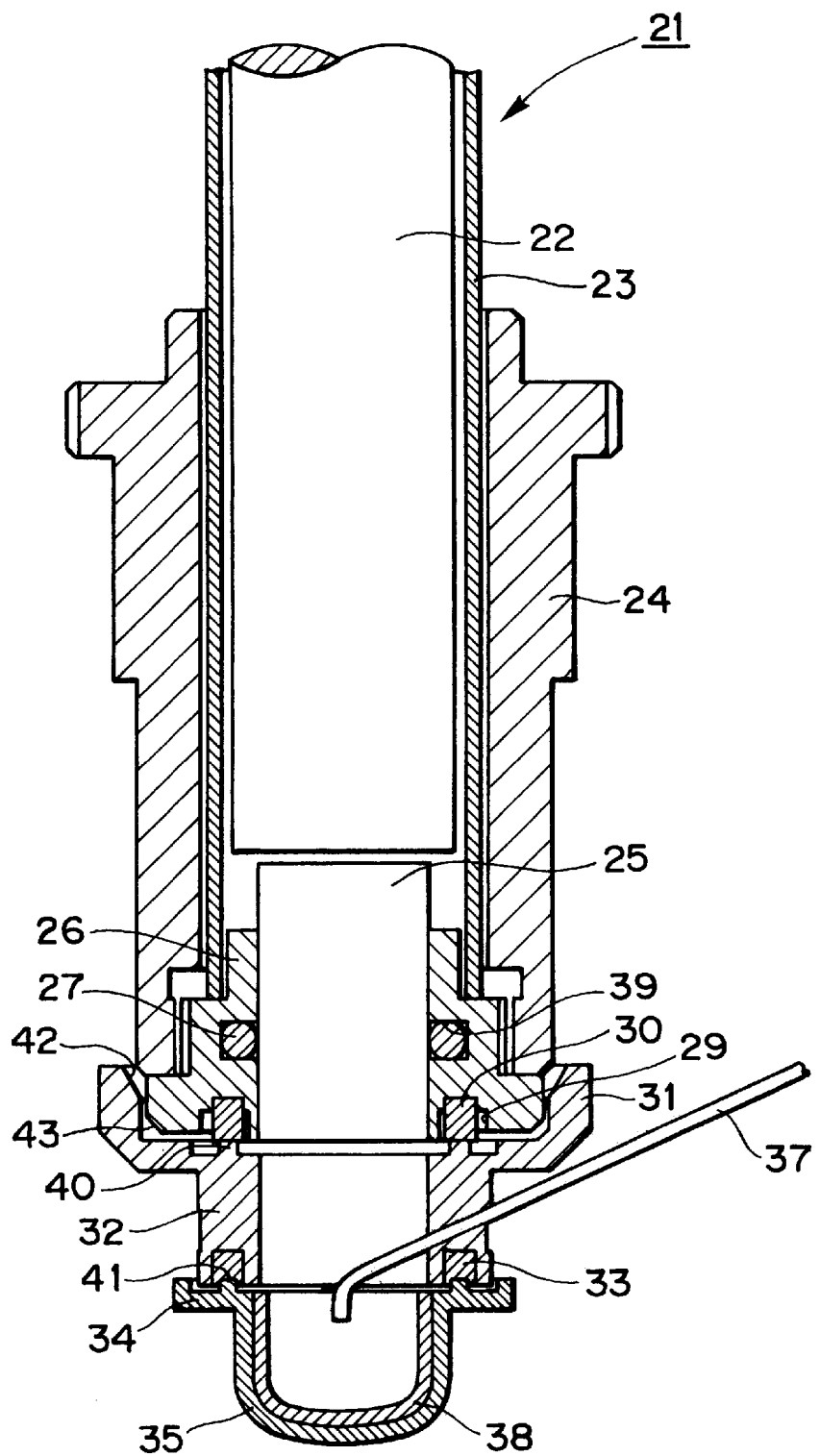
FIG. 5 is a cross section showing a measuring apparatus as another embodiment of this invention.

Next, the second embodiment of this invention will be described by referring to FIG. 5.

The measuring apparatus of this embodiment includes a shield case 24 for accommodating a PMT 22 and an optical means 25 in a light shielded state, with the optical means 25 installed on an incident axis of the PMT 22 and spaced a predetermined small distance from the PMT 22; a nozzle holder 32 shielded from external light; a coupling portion 31 provided to the upper end of the nozzle holder 32 and engaging the lower end of the shield case 24; and a supply nozzle 37 extending from outside through the side wall of the nozzle holder 32 to reach a container. The device also has a container holder 35 for a container 38 which has a coupling portion 34 engaging the lower end of the shield case 24 for the light measuring portion or the lower end of the nozzle holder 32. The container 38 is formed of, for example, a reflective, white engineering plastics and is accommodated in the container holder 35.

Here, the optical means 25 may be a refractivity-distributed, cylindrical lens, a transparent body with uniform refractivity, combined transparent bodies with different refractivities, optical fibers bundled together, a normal lens, or a combination of these.

This construction can reliably send weak light produced in the container 38 to the PMT 22, the light measuring portion, by total reflection, refraction or transmission without any leakage.

The optical means may be installed in a region inside the nozzle holder 32 that is sufficiently remote from the surface of the container 38 so that it is not exposed to liquid from the container 38, for example, in the upper part of the nozzle holder 32.

This enables the light to enter the PMT 22 more reliably.

Below the shield case 24 is provided a cover 26 that supports the optical means and seals the lower end of the shield case 24. The cover 26 is formed with an annular groove 39 opening perpendicularly to the axis in a radial direction and with an annular groove 29 opening downwardly along the axis. The annular groove 39 is fitted with an O-ring 27 to support the optical means 25. Installed in the annular groove 29 is a light shielding ring 30 made of an elastic member that keeps in the light-shielded condition the coupling portion between the nozzle holder 32 and the shield case 24 or the coupling portion between the container holder 35 or the container 38 and the shield case 24.

When the coupling portion is connected, the light shielding ring 33 is collapsed by an annular raised portion 40 of the nozzle holder 32 or by an annular raised portion 41 of the container holder 35, thus enhancing the light shielding performance.

Further, in this embodiment, because a lower edge 43 of the cover 26 below the shield case 24 and an inner edge 42 of the coupling portion 31 at the upper end of the nozzle holder 32 are chamfered, the nozzle holder, when installed, can be correctly positioned by the contact between the lower edge 43 and the inner edge 42 without requiring an accurate position control.

A cylindrical body 23 installed inside the shield case 24 is made of a material that shields particle rays such as electrons and protons and cosmic rays such as radioactive rays, for example permalloy. This assures an increased precision in measurement.

In this embodiment, too, the nozzle holder 32 is mounted or dismounted to and from the measuring apparatus by a holder mounting device not shown according to the immunoassay to be carried out, as in the first embodiment.

It is also possible to use a container transfer device to move the container or the container holder.

In this embodiment, because the coupling portions of the shield case, the nozzle holder and the container or container holder not only engage with each other but also use the light shielding ring which is formed of an elastic material that expands when tightened for coupling, the light can be shielded perfectly allowing reliable measurements.

As described above, in the measuring apparatus of this embodiment, the container for a specimen or the container holder, the light receiving unit or shield case and/or the nozzle holder are connected together in a completely light-shielding condition, so that measurements of light in various immunoassays based on different light generating principles can be made by a single test equipment. This widens the range of reagents that can be used, increasing the versatility of this measuring apparatus, thus significantly enhancing its usefulness for users and reagent manufacturers.

I claim:

1. A measuring apparatus comprising
   a light receiving unit or a light receiving unit holder connected to a light measuring device;
   a nozzle holder holding a nozzle for injecting reagents including luminescent reagents into a container;
   a container containing a specimen or a container holder; and
   a holder mounting device for optionally mounting and dismounting, according to an inspection to be performed, the nozzle holder to and from between the light receiving unit or light receiving unit holder and the container or container holder;

wherein when the nozzle holder is mounted, the light receiving unit or light receiving unit holder, the nozzle holder, and the container or container holder are coupled together to form an enclosed space and wherein when the nozzle holder is dismounted, the light receiving unit or light receiving unit holder and the container or container holder are coupled together to form an enclosed space.

2. A measuring apparatus according to claim 1, wherein the container or container holder, light receiving unit or light receiving unit holder, and the nozzle holder each include at least one light shielding means selected from the group consisting of coated with a light shielding film, made of an opaque material with an excellent light shielding characteristic, or installed in a dark room or box.

3. A measuring apparatus according to claim 1, wherein a coupling portion between the container or container holder and the light receiving unit or light receiving unit holder, or between the container or container holder and the nozzle holder, and a coupling portion between the nozzle holder and the light receiving unit or light receiving unit holder are provided with a light shielding packing.

4. A measuring apparatus according to claim 1, wherein at least one of the container or container holder, the nozzle holder, and the light receiving unit or light receiving unit holder includes a reflection means selected from the group consisting of a reflective film coating, made of a reflective material, and a reflective colored inner wall.

5. A measuring apparatus according to claim 1, wherein when the inspection to be performed is a chemical luminescence immunoassay, the nozzle holder holding a nozzle for injecting a trigger reagent is mounted, and when the inspection is a chemical luminescence enzyme immunoassay that measures light produced by an enzyme-substrate liquid reaction, the nozzle holder is dismounted.

6. A measuring apparatus according to claim 1, wherein the nozzle holder is provided with a plurality of nozzles.

7. A measuring apparatus according to claim 1, further comprising a container transfer device for transferring the container.

8. A measuring apparatus according to claim 1, wherein a photomultiplier is used as the light measuring device.

9. A measuring apparatus according to claim 1, further comprising a nozzle holder transfer device for transferring the nozzle holder.

10. A measuring apparatus according to claim 1, further comprising an engagement portion provided at an upper end of the container or container holder and adapted to engage a lower end of the light receiving unit or light receiving unit holder or a lower end of the nozzle holder, and an engagement portion provided at an upper end of the nozzle holder and adapted to engage a lower end of the light receiving unit or light receiving unit holder.

11. A measuring apparatus according to claim 1, wherein a light transmission means or a light gathering means is installed on an axis of incidence of the light measuring device in the light receiving unit holder or in the nozzle holder.

12. A measuring apparatus comprising:

a light shielding case for accommodating a photomultiplier and an optical means disposed on an incident axis of the photomultiplier so that the photomultiplier and optical means are shielded from light;

a nozzle holder shielded from external light, the nozzle holder having an engagement portion at an upper end thereof and a reagent supply nozzle, the engagement portion being adapted to engage a lower end of the light shielding case, the reagent supply nozzle piercing through a side wall of the nozzle holder from outside and reaching a container;

a light-shielded container having an engagement portion at an upper end thereof to engage a lower end of the light shielding case or a lower end of the nozzle holder, the container being formed of a reflective material or applied with a reflective color or coating, and a holder mounting device for optionally mounting and dismounting according to an inspection to be performed, the nozzle holder to and from between light shielding case and the container or container holder;

wherein, when the nozzle holder is mounted, the light shielding case, the nozzle holder, and the container or container holder are coupled together to form an enclosed space and wherein when the nozzle holder is dismounted, the light shielding case and the container or container holder are coupled together to form and an enclosed space.

13. A measuring apparatus according to claim 12, wherein the optical means is formed by a light transmission means or a light gathering means, or a combination of these.

14. A measuring apparatus according to claim 13, wherein a lower end portion of the light shielding case or the nozzle holder is formed with an annular groove, a packing formed of an annular elastic member is installed in the annular groove, and an upper end portion of the nozzle holder or the container or the container holder is formed with an annular projection to press against the packing.

15. A measuring apparatus comprising:

a light receiving unit or a light receiving unit holder connected to a light measuring device;

a rotatable nozzle holder holding a nozzle for injecting reagents including luminescent reagents into a container; and a container containing a specimen or a container holder;

wherein, when the rotatable nozzle holder is rotated to engage the light receiving unit or light receiving unit holder and the container or container holder, an enclosed space shielded from external light is formed comprising the container or container holder, rotatable nozzle holder and the light receiving unit or light receiving unit holder, and when the rotatable nozzle holder is rotated to disengage the light receiving unit or light receiving unit holder and the container or container holder, an enclosed space shielded from external light is formed comprising the container or container holder and the light receiving unit or light receiving unit holder.

* * * * *